United States Patent
Penna

(10) Patent No.: US 9,179,913 B2
(45) Date of Patent: Nov. 10, 2015

(54) SURGICAL FASTENING APPARATUS WITH DIRECTED OVERCRIMP

(75) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 720 days.

(21) Appl. No.: 13/422,278

(22) Filed: Mar. 16, 2012

(65) Prior Publication Data

US 2013/0240595 A1    Sep. 19, 2013

(51) Int. Cl.
*A61B 17/068*    (2006.01)
*A61B 17/072*    (2006.01)
*A61B 17/115*    (2006.01)
*A61B 17/064*    (2006.01)

(52) U.S. Cl.
CPC ....... *A61B 17/07207* (2013.01); *A61B 17/1155* (2013.01); *A61B 17/0644* (2013.01)

(58) Field of Classification Search
CPC .............................. A61B 17/068; A61B 17/08
USPC .......... 227/175.1, 176.1, 178.1, 179.1, 180.1; 411/457, 923; 606/153, 219
See application file for complete search history.

(56) References Cited

U.S. PATENT DOCUMENTS

| | | |
|---|---|---|
| 4,589,582 A | 5/1986 | Bilotti |
| 4,805,823 A | 2/1989 | Rothfuss |
| 5,221,036 A | 6/1993 | Takase |
| 5,350,400 A * | 9/1994 | Esposito et al. ............. 606/219 |
| 5,480,089 A | 1/1996 | Blewett |
| 5,630,540 A * | 5/1997 | Blewett ...................... 227/176.1 |

(Continued)

FOREIGN PATENT DOCUMENTS

| | | |
|---|---|---|
| EP | 1 728 473 | 12/2006 |
| EP | 2 116 192 | 11/2009 |

(Continued)

OTHER PUBLICATIONS

Extended European Search Report corresponding to EP 13 15 9355.0, completed Mar. 7, 2014 and mailed Mar. 17, 2014; (8 pp).

(Continued)

*Primary Examiner* — Hemant M Desai
*Assistant Examiner* — Nathaniel Chukwurah

(57) ABSTRACT

A surgical fastener applier is disclosed, including a surgical fastener forming apparatus including surgical fasteners, an anvil having a plurality of fastener deforming cavities, and a plurality of pushers. The fastener includes a backspan having a bend along its length, and a pair of legs extending from the ends of the backspan. The pusher is configured to support the backspan, and translate the surgical fastener toward the fastener deforming cavities. The fastener legs enter and are deformed by the cavities in a manner such that they exit the cavities and contact a forming head protruding from the pusher. The forming head curves a portion of the fastener legs such that they lie parallel to and abut a portion of the backspan in the same plane. Also disclosed is a method of forming a surgical fastener with the surgical fastener forming apparatus.

9 Claims, 16 Drawing Sheets

(56) References Cited

U.S. PATENT DOCUMENTS

| | | | |
|---|---|---|---|
| 5,749,896 A | 5/1998 | Cook | |
| 6,638,297 B1 * | 10/2003 | Huitema | 606/219 |
| 6,953,138 B1 | 10/2005 | Dworak et al. | |
| 7,398,907 B2 | 7/2008 | Racenet et al. | |
| 7,673,781 B2 | 3/2010 | Swayze et al. | |
| 7,673,782 B2 | 3/2010 | Hess et al. | |
| 7,722,610 B2 * | 5/2010 | Viola et al. | 606/250 |
| 7,735,703 B2 | 6/2010 | Morgan et al. | |
| 7,794,475 B2 * | 9/2010 | Hess et al. | 606/219 |
| 7,815,092 B2 | 10/2010 | Whitman et al. | |
| 7,934,630 B2 | 5/2011 | Shelton, IV et al. | |
| 8,008,598 B2 | 8/2011 | Whitman et al. | |

FOREIGN PATENT DOCUMENTS

| | | |
|---|---|---|
| WO | WO 02/19920 | 3/2002 |
| WO | WO 2009/005969 | 1/2009 |

OTHER PUBLICATIONS

European Office Action corresponding to EP 13 159 355.0 dated Jun. 23, 2015; 3 pp.

* cited by examiner

SURGICAL FASTENING APPARATUS WITH DIRECTED OVERCRIMP

BACKGROUND

1. Technical Field

The present disclosure relates to surgical fasteners. More particularly, the present disclosure relates to surgical fasteners for use with surgical fastening instruments for joining tissue segments of varying thicknesses.

2. Background Of Related Art

Surgical fasteners and appliers are well known in the surgical arts and have become critical to many life saving surgical procedures. The use of surgical fastener appliers for applying fasteners to join tissue or tissue segments in a fast and efficient manner has obviated the time consuming step of manual suturing of tissue or tissue segments in a variety of surgical procedures, e.g., anastomoses procedures. The reduced time required to perform these surgical procedures using surgical fastener appliers has resulted in reduced trauma and risk to patients.

Typically, a surgical fastener includes a backspan and a pair of spaced legs. The legs are driven through tissue and into an anvil to deform the fastener into a desired configuration, e.g., a B-staple, to join segments of tissue, seal an incision or wound, and effect hemostasis of tissue or tissue segments. One concern associated with current surgical fasteners surrounds that the manner in which the fastener legs deform. It is desirable to provide a surgical fastener that deforms in a controlled manner to dispose the fastener legs in such a way that the surgical fastener has a minimal profile. Such a surgical fastener will secure sections of tissue together while having a minimal interference with the natural shifting of surrounding tissue.

SUMMARY

According to one aspect of the present disclosure, a surgical fastener applier for applying a plurality of fasteners to body tissue is provided. The surgical fastener applier includes a handle assembly, an elongate body, a disposable loading unit and a drive member. The disposable loading unit includes a tool assembly having a cartridge assembly and an anvil assembly disposed on respective opposable jaws. The cartridge assembly includes a plurality of surgical fasteners and the anvil assembly includes a plurality of fastener deforming cavities. The surgical fastener applier includes a surgical fastener forming apparatus that includes the surgical fasteners, the pushers, and the anvil having the plurality of fastener deforming cavities.

The surgical fastener includes a backspan having a bend along its length, the backspan and bend defining a horizontal plane "H". A pair of fastener legs extends from the backspan. The legs may be substantially perpendicular to the backspan, or may be disposed at another angle. The legs terminate at tips that may be sharpened, blunt, or otherwise configured.

A pusher includes a groove configured to support the backspan of the surgical fastener such that upon translation of the pusher, the fastener is approximated toward the anvil. Laterally spaced from the groove and protruding from the pusher is a forming head defined by a pair of opposing curves.

The fastener deforming cavities of the anvil are configured to receive the surgical fasteners. The fastener deforming cavities are disposed in spaced pairs that oppose the legs of the surgical fasteners, and are generally arcuate in profile. Each cavity has first and second ends, with the second ends exiting opposite the curves of the forming head.

Upon actuation of an actuation mechanism, the opposed jaws of the surgical fastener applier are approximated and capture one or more layers of tissue therebetween. Continued actuation of the actuation mechanism translates a sled distally through the fastener cartridge. As the sled moves through the fastener cartridge, camming surfaces on the sled engage camming surfaces on the pushers thereby urging the pushers towards the anvil disposed in the opposing jaw. The pushers move the fasteners towards the fastener deforming cavities of the anvil. The legs of each fastener contact the surface of the first end its respective fastener deforming cavity, deform in a manner defined by the profile of the cavity, and exit the second end of the fastener deforming cavity. Upon exiting the second end of the respective fastener deforming cavity, each fastener leg engages the curves of the forming head and further deforms to lie parallel to and abut the backspan in the horizontal plane H. The fastener legs and tips are thus disposed such that interference with surrounding tissue is minimized. In a further aspect of the present disclosure, the fastener tips are contoured to engage a portion of the backspan after formation.

According to another aspect of the present disclosure, an annular surgical fastener applier system includes an annular surgical fastener applier having a handle assembly and a cartridge assembly operably connected to the handle assembly and including a plurality of pushers. Each of the plurality of pushers includes a protruding forming head and a groove thereon. The surgical fastener applier also includes an anvil assembly operably connected to the handle assembly and including a plurality of fastener deforming cavities, each of the plurality of fastener deforming cavities having an arcuate profile. The surgical fastener applier system additionally includes a plurality of surgical fasteners arranged in at least one annular row, each of the plurality of surgical fasteners including a backspan and a pair of legs extending therefrom, the backspan having a bend. Each of the plurality of surgical fasteners is configured for engagement by the groove of each of the plurality of pushers, and the cartridge assembly and the anvil assembly are configured for approximation toward each other such that the plurality of pushers align the legs of each of the plurality of surgical fasteners for entry into the respective fastener deforming cavities, and a portion of the forming head of each of the plurality of pushers is level with the groove of each of the plurality of pushers.

According to another aspect of the present disclosure, the protruding forming head of each of the plurality of pushers includes a curved surface. In a further aspect of the present disclosure, the protruding forming head of each of the plurality of pushers and each of the plurality of fastener deforming cavities are disposed on opposing surfaces of the cartridge assembly and the anvil assembly, respectively. In another aspect of the present disclosure, each of the plurality of pushers are configured for movement relative to the cartridge assembly. In a further aspect of the present disclosure, the legs of each of the plurality of surgical fasteners are deformable. In yet a further aspect of the present disclosure, the cartridge assembly has a cylindrical configuration.

These and other features of the current disclosure will be explained in greater detail in the following detailed description of the various embodiments.

BRIEF DESCRIPTION OF THE DRAWINGS

Various embodiments of the presently disclosed surgical fastening apparatus are disclosed herein with reference to the drawings, wherein.

DETAILED DESCRIPTION OF EMBODIMENTS

Embodiments of the presently disclosed surgical fastening apparatus will now be described in detail with reference to the drawings wherein like numerals designate identical or corresponding elements in each of the several views.

Figure 1:
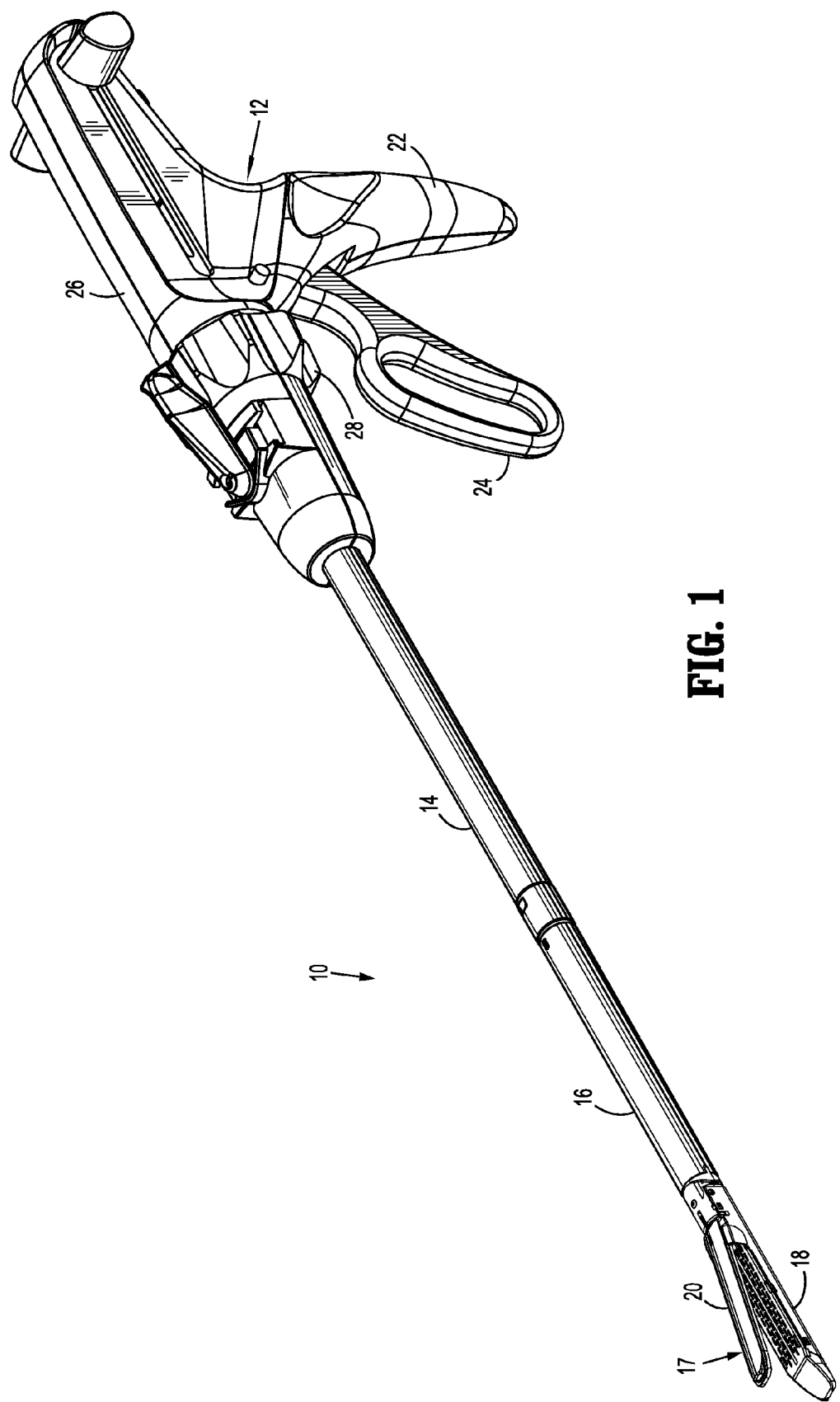
FIG. 1 is a perspective view of a surgical fastener applier.
Figure 2:
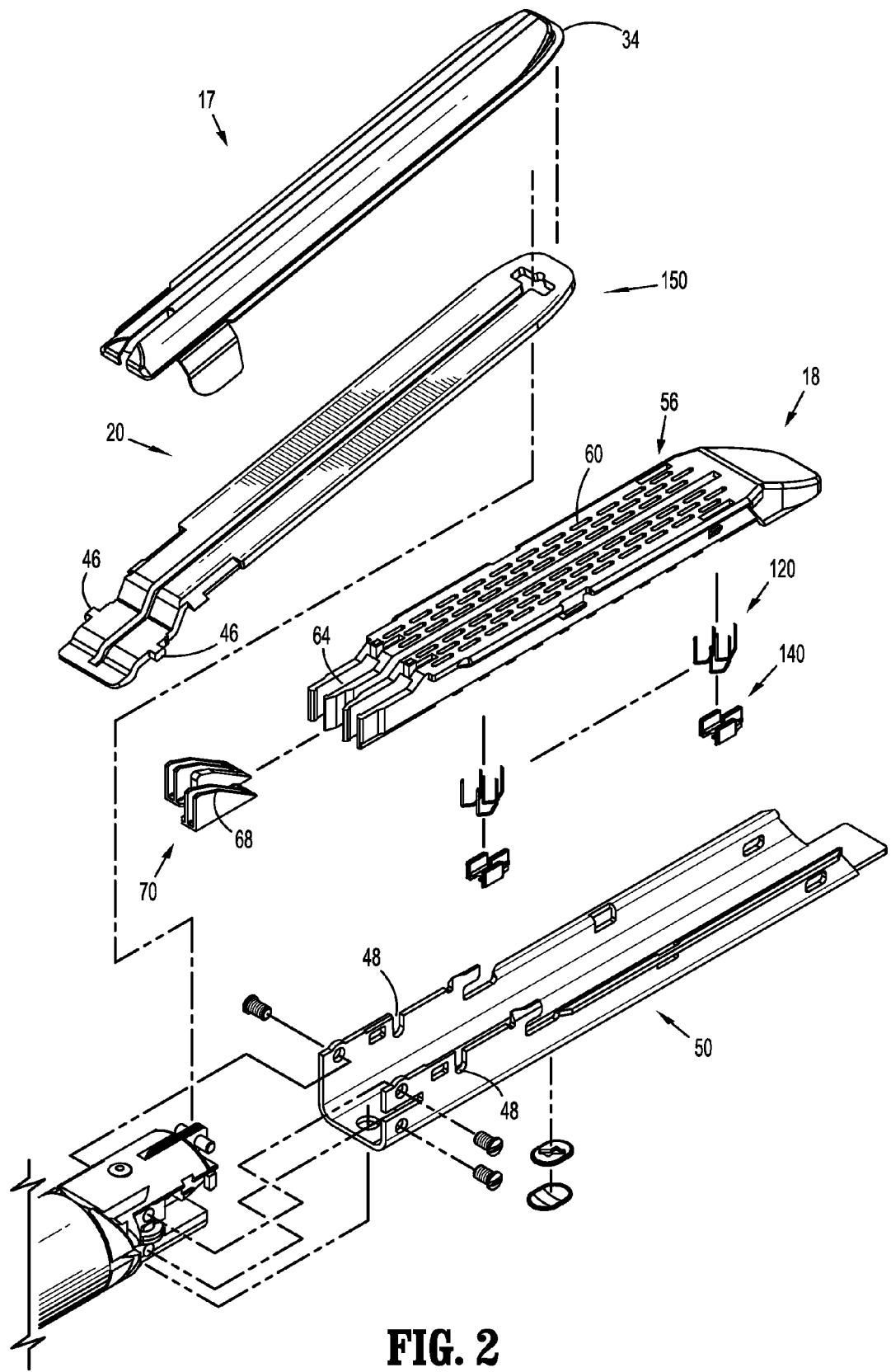
FIG. 2 is a perspective view of the tool assembly of the surgical fastener applier of FIG. 1 with parts separated.
Figure 3:
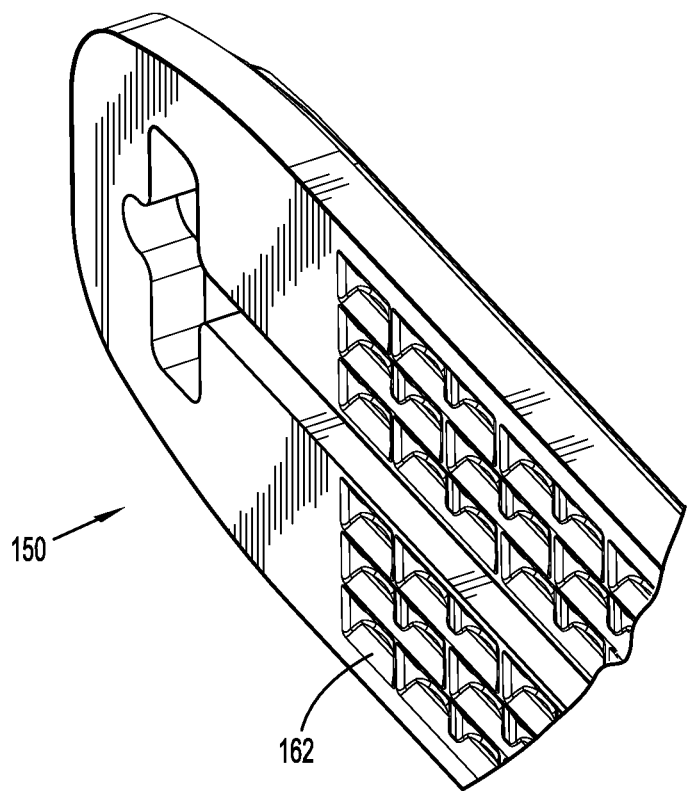
FIG. 3 is an enlarged perspective view of the distal end of the anvil assembly showing a plurality of fastener deforming cavities.
Figure 4:
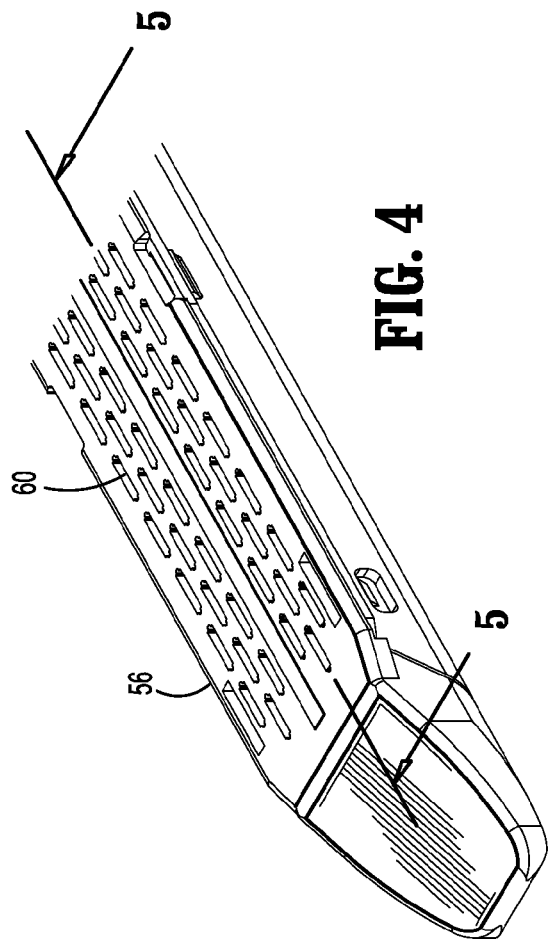
FIG. 4 is an enlarged perspective view of the distal end of the fastener cartridge of the surgical fastener apparatus shown in FIG. 1.
Figure 5:
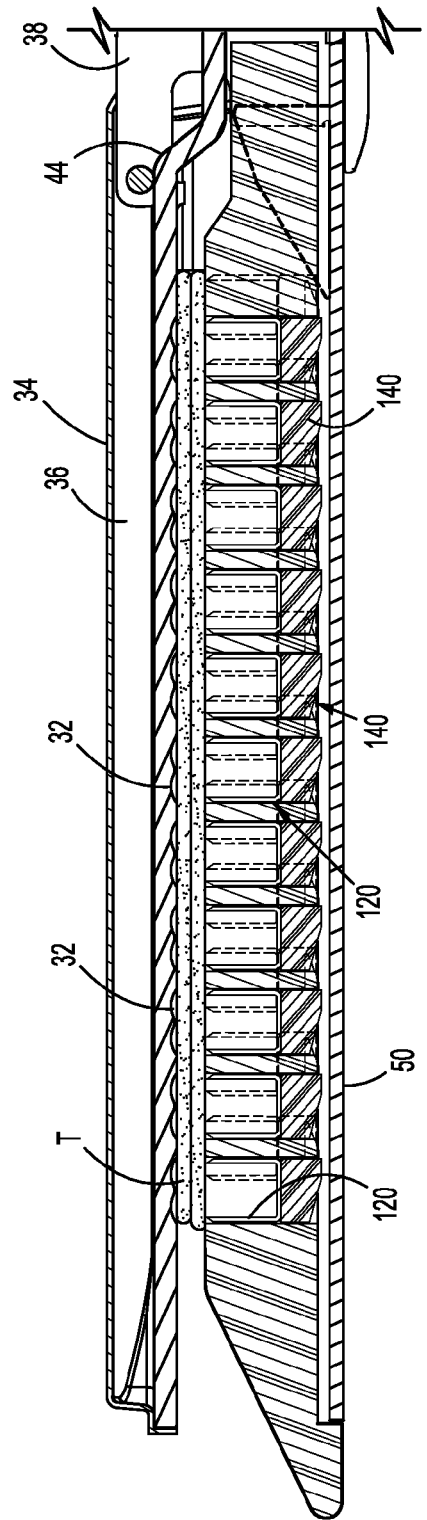
FIG. 5 is a cross-sectional view taken along section line 5-5 of FIG. 4.

Referring initially to FIG. 1, an embodiment of the presently disclosed surgical fastener applier 10 is shown. Briefly, surgical fastener applier 10 includes a handle assembly 12 and an elongated body 14. A disposable loading unit or DLU 16 is releasably secured to a distal end of elongated body 14. Disposable loading unit 16 includes a tool assembly 17 having a cartridge assembly 18 housing a plurality of surgical fasteners 120 (FIG. 2) and an anvil assembly 20 movably secured in relation to cartridge assembly 18. Disposable loading unit 16 is configured to apply linear rows of surgical fasteners. Handle assembly 12 includes a stationary handle member 22, a movable handle member 24, and a barrel portion 26. A rotatable member 28 is preferably mounted on the forward end of barrel portion 26 to facilitate rotation of elongated body 14 with respect to handle assembly 12. Other surgical fastener appliers of the general type disclosed are disclosed in U.S. Pat. Nos. 5,040,715; 5,307,976; 5,312,023; 5,318,221; 5,326,013; and 5,332,142, the entire contents of which are incorporated by reference herein.

Referring to FIGS. 2-7, tool assembly 17 preferably includes anvil assembly 20 and cartridge assembly 18. Anvil assembly 20 includes anvil portion 150 having a plurality of fastener deforming cavities 162 and a cover plate 34 secured to a top surface of anvil portion 150 to define a cavity 36 therebetween. Cover plate 34 is provided to prevent pinching of tissue during clamping and firing of surgical fastener applier 10 (FIG. 1). Cavity 36 is dimensioned to receive a distal end of a driving member 38 in mechanical communication with the handle assembly 12 (FIG. 1). Upon actuation of the handle assembly 12, driving member 38 is driven distally through the elongate body 14 (FIG. 1) and translates into a portion of the cavity 36, as shown. A camming surface 44 formed on anvil portion 150 is positioned to engage drive member 38 to facilitate clamping of tissue T. A pair of pivot members 46 formed on anvil portion 150 is positioned within slots 48 formed in carrier 50 to guide the anvil portion 150 between the open and clamped positions.

Fastener cartridge 56 includes retention slots 60 for receiving a plurality of fasteners 120 and pushers 140. A plurality of spaced apart longitudinal slots 64 extends through fastener cartridge 56 to accommodate upstanding cam wedges 68 of actuation sled 70. During operation of surgical fastener applier 10, drive member 38 translates actuation sled 70 through longitudinal slots 64 of fastener cartridge 56 to advance cam wedges 68 into sequential contact with pushers 140, to cause pushers 140 to translate vertically within slots 60 and urge surgical fasteners 120 from slots 60 into the fastener deforming cavities 162 of anvil assembly 20. The particular configurations of fasteners 120, pushers 140, and fastener deforming cavities 162 determine the final disposition of fasteners 120 within tissue T, as will be discussed further below.

Figure 11:
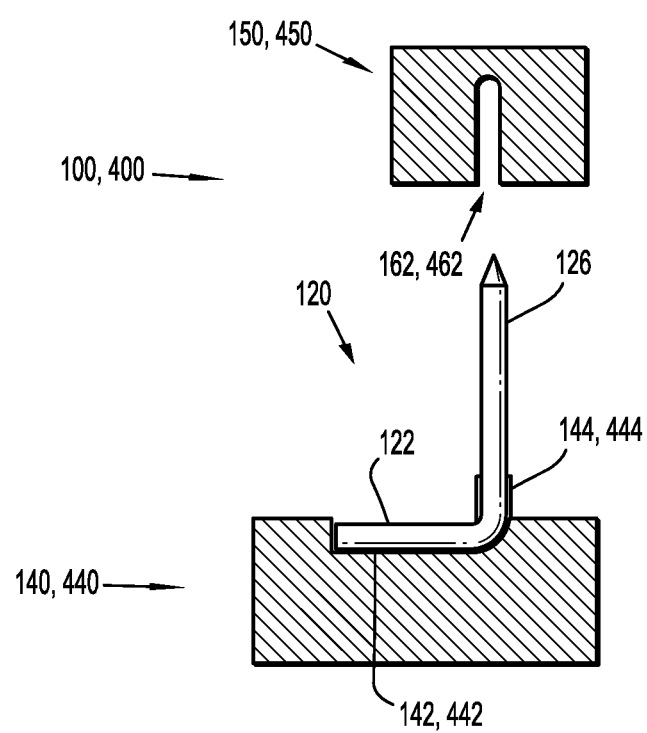
FIG. 11 is a cut-away view of the surgical fastener, supported by a pusher and opposing a pair of fastener deforming cavities.

Turning now to FIG. 11, fastener forming apparatus 100 is shown in cross-section. Fastener forming apparatus 100 includes surgical fasteners 120, pushers 140, and a section of anvil portion 150 having fastener deforming cavities 162. While fastener forming apparatus 100 is integrated into the cartridge assembly 18 (FIG. 2) and anvil assembly 20 (FIG. 2) of surgical fastener applier 10 (FIG. 2) as described above, fastener deforming apparatus 100 will hereafter be discussed with respect to a single surgical fastener 120, pusher 140, and a section of anvil portion 150 containing a pair of fastener deforming cavities 162 for clarity.

Figure 8:
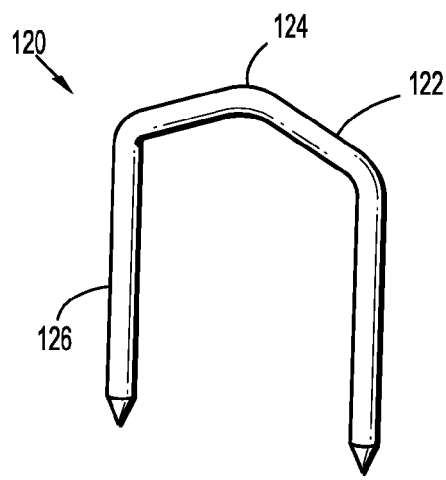
FIG. 8 is a perspective view of the surgical fastener.
Figure 10:
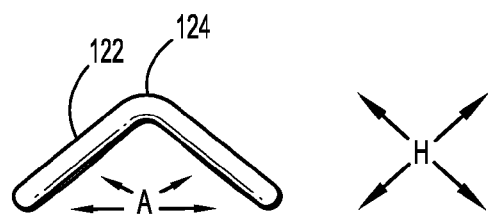
FIG. 10 is a bottom plan view of the surgical fastener.

Turning now to FIG. 8, surgical fastener 120 includes a backspan 122 having a bend 124 along its length. While the bend 124 is shown as being formed in a central portion of the backspan 122, other placements for the bend 124 along the length of backspan 122 are contemplated. The bend 124 may be formed by deforming backspan 122 during or after manufacture, or prior to use. Additionally, the bend 124 may be a curve having a radius, as shown, or may be angular, squared, or any desirable shape or cross section. The backspan 122 and bend 124 define a horizontal plane "H" (FIG. 10). One or more legs 126 extend outwardly from plane H and the backspan 122. As shown, legs 126 may extend from backspan 122 such that they are substantially perpendicular to plane H, or may be disposed at an angle with backspan 122. Legs 126 may extend from ends of backspan 122, or may be placed at other locations on the backspan 122. The point at which the legs 126 meet the backspan 122 may generally form a rounded edge or shoulder, as shown.

Figure 9:
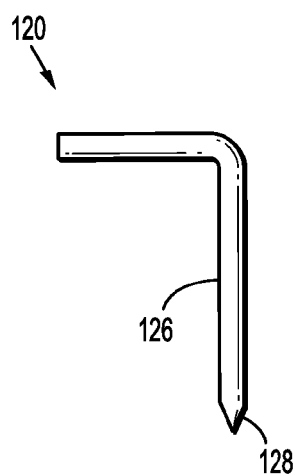
FIG. 9 is a side view of the surgical fastener.

Referring to FIG. 9, the surgical fastener 120 is shown in side view. Legs 126 may be straight and have a substantially circular cross-section, or may have any other desirable shape or cross-sectional profile. Legs 126 terminate in fastener tips 128. Fastener tips 128 may be sharpened points as shown, or may be tapered, blunt, serrated, or have any other desirable configuration.

Turning to the bottom plan view of FIG. 10, the profile of backspan 122 can be seen. The backspan 122 and bend 124 define an area "A" within plane H that will accommodate portions of legs 126 upon deformation, as will be discussed further below. The portions of backspan 122 extending away from bend 124 may be substantially straight and have a circular cross-sectional profile as shown, or may have any other desirable shape or cross-sectional profile.

Referring to FIG. 11, surgical fastener 120 is shown supported by pusher 140 and opposing a section of anvil portion 150 containing a pair of fastener deforming cavities 162. Pusher 140 contains a groove 142 for supporting backspan 122. Groove 142 is shaped to accommodate the profile of backspan 122, and will retain the backspan 122 upon motion or moderate lateral shifting, but will disengage from backspan 122 when translated away from backspan 122.

Figure 12:
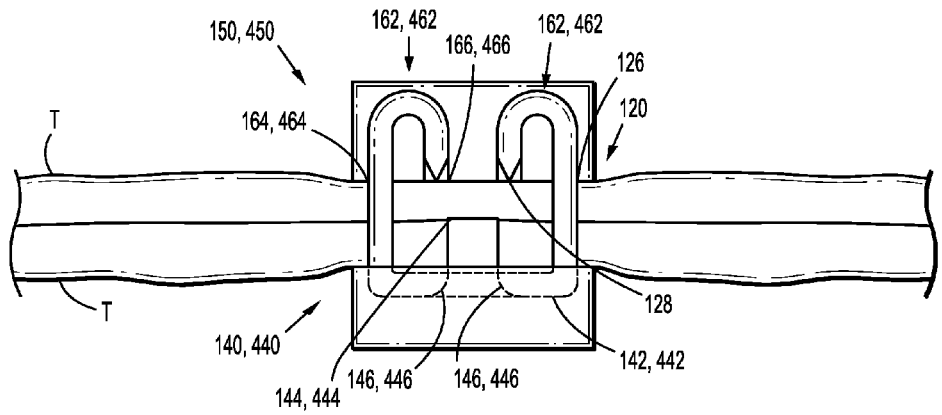
FIG. 12 is a cut-away view of the anvil section, fastener, and pusher of FIG. 11, with the pusher loaded with the fastener and partially engaged with the fastener deforming cavities, and penetrating a layer of tissue.

Turning to FIG. 12, a forming head 144 is laterally spaced from groove 142 and extends from the surface of pusher 140. Forming head 144 includes curved portion 146 that engage legs 126 upon fastener formation, as will be described further below. Curved portion 146 extend partially through the proximal portion of pusher 140 such that the distal portion of curved portion 146 approach the distal surface of groove 142. The distal portions of curved portion 146 lie substantially level with the groove 142 such that the distal portions of curved portion 146 lie coplanar with and parallel to the backspan 122.

Anvil portion 150 contains fastener deforming cavities 162 to receive legs 126. Fastener deforming cavities 162 have a first end 164 and a second end 166. Fastener deforming cavities 162 generally have an arcuate profile, though may have any shape or configuration to accommodate the desired fastener formation. The arcuate profile of fastener deforming cavities 162 is such that the first end 164 of each cavity 162 is opposed to a respective curve 146.

Figure 6:
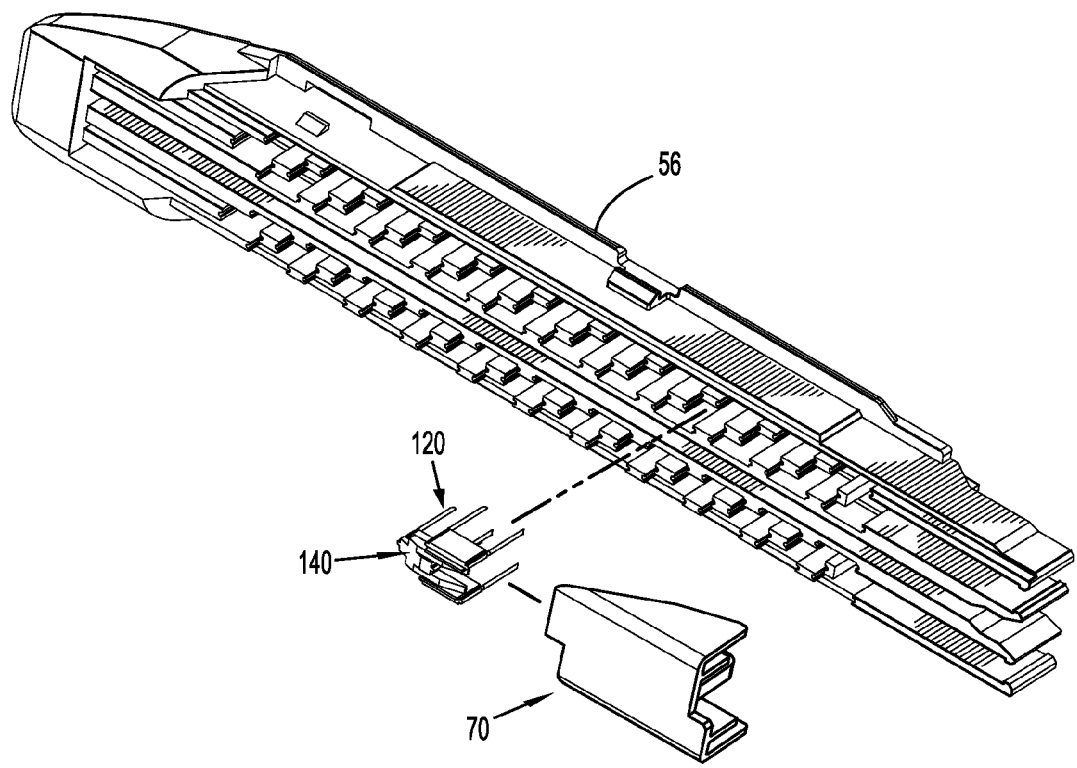
FIG. 6 is a bottom perspective view of the fastener cartridge shown in FIG. 2, along with a pusher and a surgical fastener.
Figure 7:
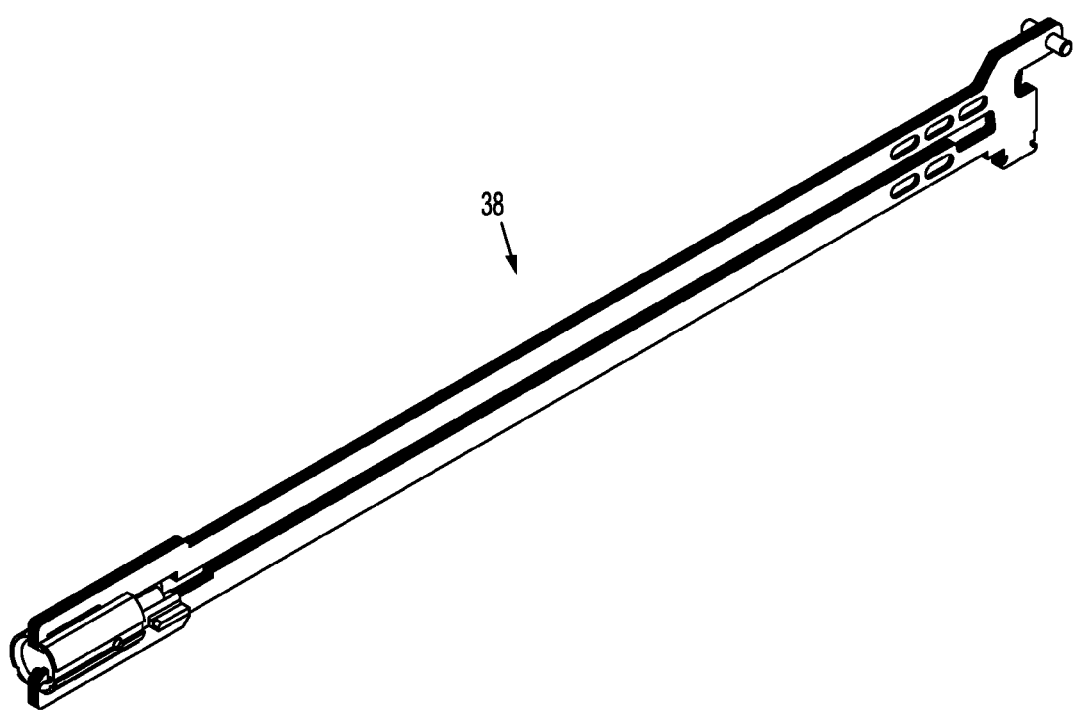
FIG. 7 is a perspective view of a drive member.

Referring briefly to FIG. 6, as the driving member 38 (FIG. 7) translates actuation sled 70 through longitudinal slots 64 of fastener cartridge 56, cam wedges 68 (FIG. 2) cause pushers 140 to translate vertically within slots 60 and urge fasteners 120 toward fastener deforming cavities 162 (FIG. 12) such that legs 126 deform in a manner defined by the profile of fastener deforming cavities 162. Tips 128 (FIG. 12) ultimately exit the second end 166 (FIG. 12) of cavities 162.

Figure 13:
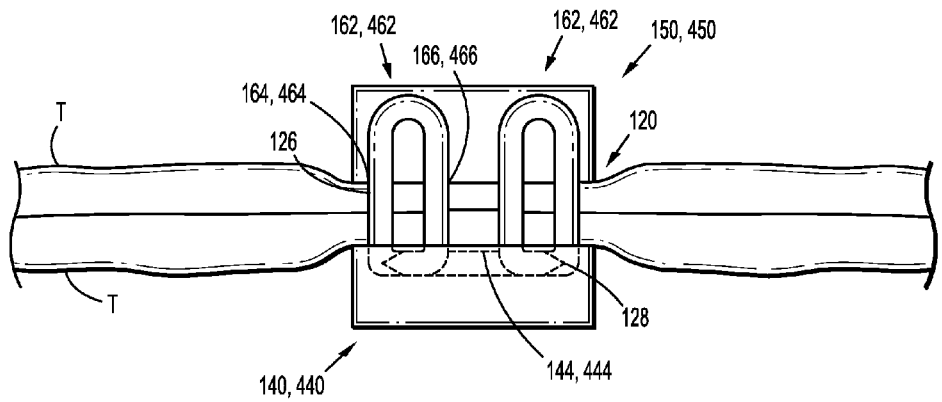
FIG. 13 is the cut-away view of FIG. 12, with the fastener legs being deformed.

Referring to FIGS. 12 and 13, the deformation of fastener 120 is shown. As the pusher 140 and anvil section 150 are drawn together, the tips 128 and portions of legs 126 again penetrate tissue T and engage curved portion 146 and further deform away from forming head 144. As the legs 126 approach the proximal portion of the curved portion 146, they diverge and approach the ends of backspan 122 such that they lie parallel to and abut a portion of the backspan 122 in the plane H (FIG. 10).

Figure 14:
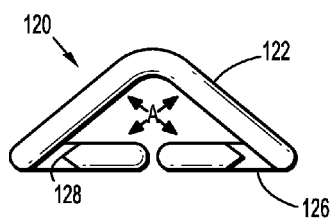
FIG. 14 is a bottom plan view of the surgical fastener after being deformed by the fastener deforming cavities and pusher curves.
Figure 15:
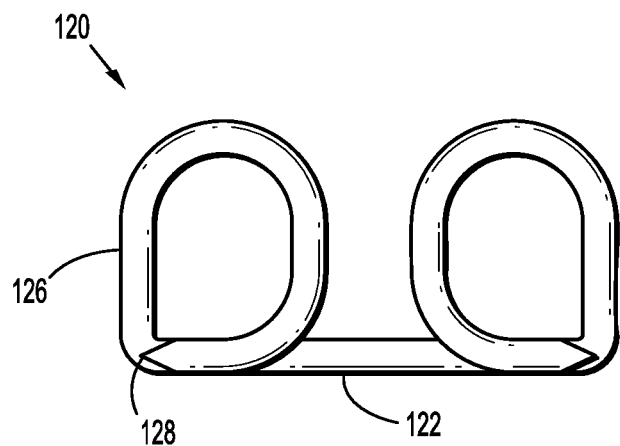
FIG. 15 is a side view of the surgical fastener after being deformed by the fastener deforming cavities and pusher curves.

Turning to FIGS. 14 and 15, the fully formed surgical fastener 120 is seen. Portions of the legs 126 lie parallel to and abut the backspan 122 within area A of the horizontal plane H (FIG. 10). The tips 128 of legs 126 face a portion of backspan 122 such that any sharp surfaces of tips 128 are oriented toward the backspan 122 as opposed to surrounding tissue.

Figure 16:
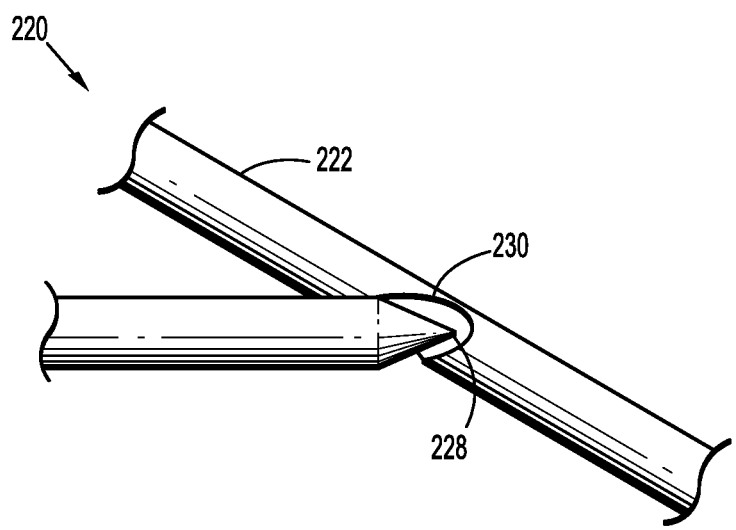
FIG. 16 is a detail view of an alternative embodiment of the surgical fastener wherein the fastener legs have a contoured surface to engage the backspan.
Figure 17:
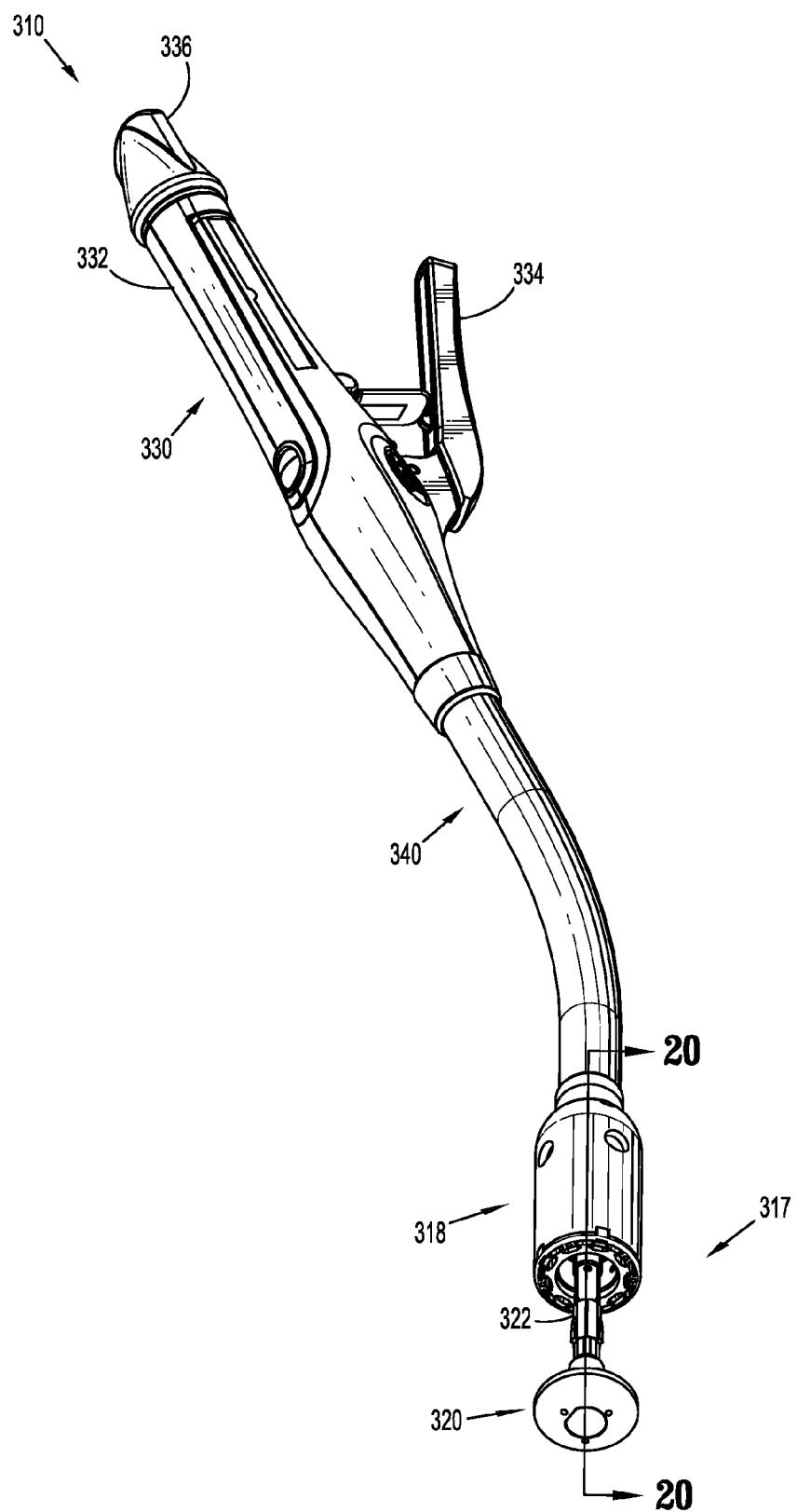
FIG. 17 is a perspective view of an alternative embodiment of a surgical fastener applier.

Referring to FIG. 16, an alternative embodiment of a surgical fastener 220 is shown. Surgical fastener 220 is substantially similar to surgical fastener 120 described above, but includes a contoured tip 228 that is configured to engage a portion of backspan 222 upon fastener formation as described above. Contoured tip 228 may have a fork, a divot, a groove, a ledge, or any suitable configuration to engage a portion of backspan 222. Further, the backspan 222 may include a notch 230 to receive contoured tip 228. The engagement of contoured tip 228 and backspan 222 further serves to isolate surrounding tissue from the sharpened surfaces of contoured tip 228, minimizing inadvertent damage and tearing with the natural shifting of tissue. It will be understood that the above-described fastener forming apparatus may be configured for use in a variety of surgical fastener appliers, such as transverse anastomosis staplers, end-to-end anastomosis staplers, laparoscopic staplers, and transverse anastomosis staplers FIG. 17 illustrates an embodiment of a surgical fastener applier according to the present disclosure, shown generally as surgical fastener applier 310. Surgical fastener applier 310, as shown, is configured to engage hollow or circular sections of tissue. Accordingly, surgical fastener applier 310 may be an annular or, alternatively, circular surgical stapler. Examples of instruments for performing circular tissue fastening operations are described in U.S. Pat. Nos. 6,053,390; 5,588,579; 5,119,987; 5,005,749; 4,646,745; 4,576,167; and 4,473,077, each of which is incorporated herein in its entirety by reference.

Surgical fastener applier 310 includes a handle assembly 330 and an elongate body 340 extending distally from handle assembly 330. A tool assembly 317 includes a cartridge assembly 318 and an anvil assembly 320, and is mounted on a distal end of elongate body 340. Handle assembly 330 includes a fixed handle 332 and a moveable handle or trigger 334. Handle assembly 330 also includes an adjustment knob 336 for moving an anvil assembly 318 relative to cartridge assembly 320. The structure and function of handle assembly 330 will only be described herein to the extent necessary to fully disclose the operation of tool assembly 317. It is envisioned that tool assembly 317 may be modified for use with any actuation assembly, powered or manual, and may be capable of two independent actuation strokes. For example, the tool assembly 317 may be configured as a removable unit that can be replaced after use, the tool assembly being attached to a handle assembly that includes one or more motors, and/ or computerized control features such as software and/or hardwired logic. In certain alternatives, the cartridge assembly 320 is removable and replaceable and the elongate body can be removable and replaceable in any of these examples. It is further envisioned that the fastener applier provides two or more independent actuation strokes, which may be completed by the same drive member completing two strokes or by two separate drive members.

Cartridge assembly 318 of tool assembly 317 is operably mounted to a distal end of elongate body 340 of surgical fastener applier 310. In one embodiment, cartridge assembly 318 is removably secured to elongate body 340 such that cartridge assembly 318, or a portion thereof, may be replaced and surgical fastener applier 310 may be reused. In another embodiment, only a portion of cartridge assembly 318 is configured to be removed, and subsequently replaced or reloaded. Alternatively, surgical fastener applier 310 may be configured for a single use, i.e., disposable. Cartridge assembly 318 and anvil assembly 320 are interconnected by an anvil shaft 322, as will be described further below.

Figure 18:
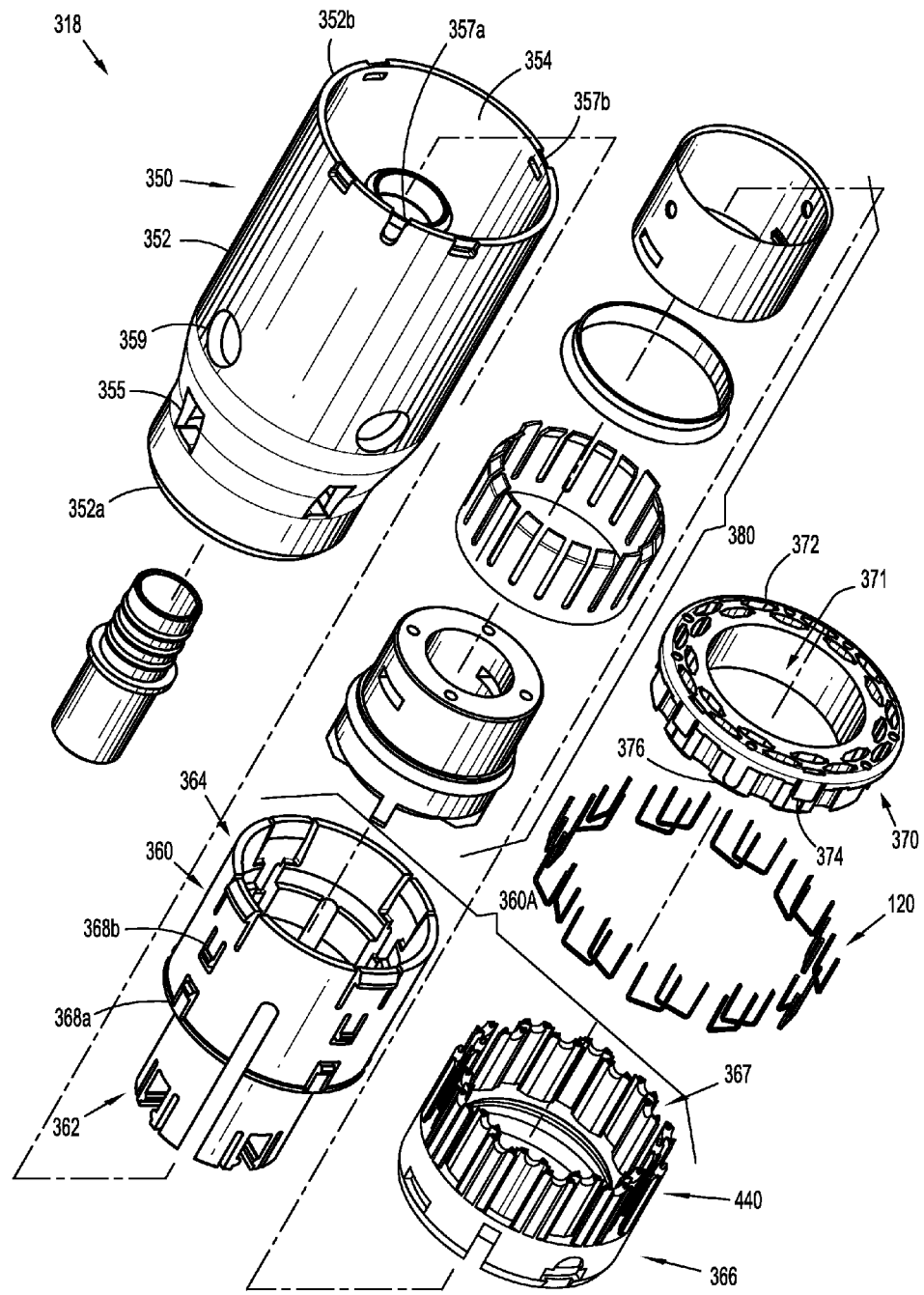
FIG. 18 is a parts-separated view of the cartridge assembly and anvil assembly of the surgical fastener applier of FIG. 17.

Turning now to FIG. 18, cartridge assembly 318 includes a housing 350, a pusher assembly 360A, a surgical fastener cartridge 370, and a knife assembly 380. The various parts are inserted through the top of the housing during assembly. Knife assembly 380 may be operable to cut or section tissue during operation of surgical fastener applier 310, as is known in the art.

A proximal end 352a of outer cylindrical portion 352 of housing 350 includes a plurality of tabs 355 formed thereon configured to operably couple cartridge assembly 318 with a distal end of elongate body 340 (FIG. 17). A distal end 352b of outer cylindrical portion 352 of housing 350 defines a plurality of recesses 357b formed thereabout configured to receive mounting tabs 374 of surgical fastener cartridge 370. Distal end 352b of outer cylindrical portion 352 of housing 350 also defines a slot 357a configured to receive a projection 376 formed on surgical fastener cartridge 370. Slot 357a is positioned such that when projection 376 is received in slot 357a, mounting tabs 374 of surgical fastener cartridge 370 are properly aligned with recesses 357b formed in outer cylindrical portion 352 of housing 350. Outer cylindrical portion 352 of housing 350 further defines a plurality of openings 359. As will be discussed in further detail below, each of the plurality of openings 359 is configured to engage a pair of a plurality of detents 368a, 368b formed on a distal portion 364 of pusher adaptor 360.

Pusher assembly 360A includes a pusher adaptor 360 and a pusher member 366. Pusher adaptor 360 is a substantially cylindrical member having a proximal portion 362 and a distal portion 364. Proximal portion 362 of pusher adaptor 360 is configured for operable engagement with a drive member (not shown). Distal portion 364 of pusher adaptor 360 is configured to operably engage pusher member 366.

Surgical fastener cartridge 370 is a substantially cylindrical member configured to operably engage distal end 352b of outer cylindrical portion 352 of housing 350 and defines a longitudinal opening 371. Surgical fastener cartridge 370 includes a plurality of surgical fastener receiving pockets 372 disposed about opening 371 arranged in two concentric rows. Surgical fastener receiving pockets 372 align with pushers 440 formed on distal portion 367 of pusher member 366. Surgical fastener cartridge 370 includes a plurality of mounting tabs 374 and also includes a protrusion 376. Mounting tabs 374 operably engage surgical fastener cartridge 370 with distal portion 352b formed in outer cylindrical portion 352 of housing 350 and protrusion 376 assures the proper alignment of surgical fastener cartridge 370 with outer cylindrical portion 352 of housing 350.

Pushers 440, as shown, are configured to engage surgical fasteners 120. Accordingly, surgical fasteners 120 are arranged in at least one annular row within cartridge assembly 318. Referring momentarily back to FIG. 8, surgical fasteners 120 are adapted for use within the circular configuration of surgical fastener applier 310 (FIG. 17) due to the bend 124 in backspan 122. In embodiments, the angle of bend 124 in backspan 122 may be modified to suit the particular needs of implementation of surgical fasteners 120.

Figure 19:
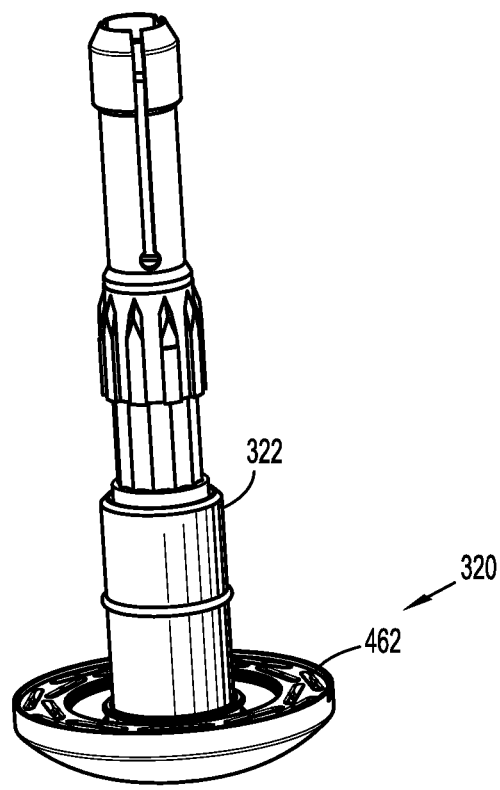
FIG. 19 is a perspective view of the anvil shaft and anvil assembly of the surgical fastener applier of FIG. 17.

Turning to FIG. 19, anvil assembly 320 is shown coupled to a distal end of anvil shaft 322. Anvil shaft 322 and anvil assembly 320 are configured for engagement with cartridge assembly 318 (FIG. 17) described above. As will be discussed further below, a proximal surface of anvil assembly 320 includes a plurality of fastener deforming cavities 462.

Figure 20:
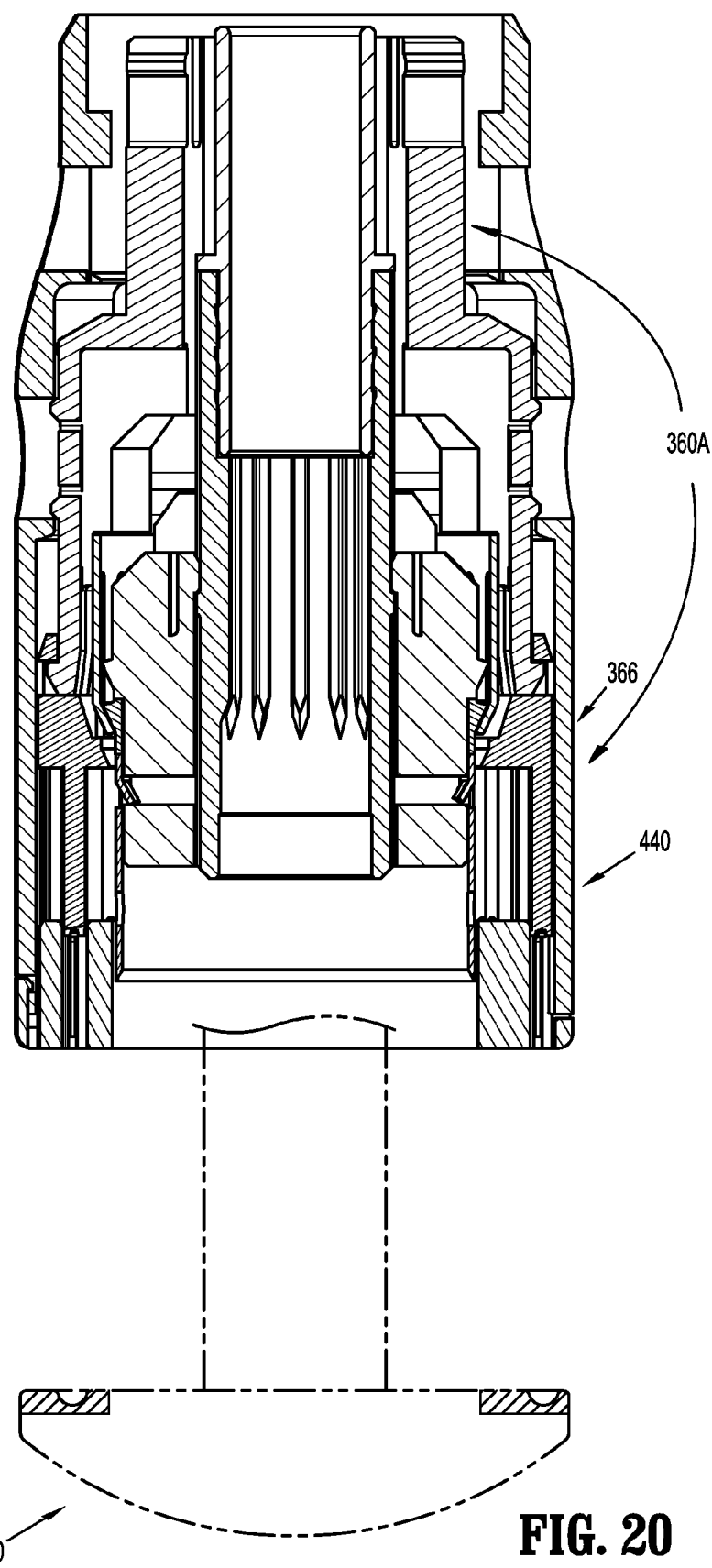
FIG. 20 is a cross-sectional view taken along section line 20-20 of FIG. 17.

The operation of cartridge assembly 318 will now be described with reference to FIGS. 18-21. Referring initially to FIGS. 18 and 20, cartridge assembly 318 is shown in a first or initial condition. In the initial condition, pusher assembly 360A is received between outer and inner cylindrical portions 352, 354 of housing 350. Surgical fastener cartridge 370 is in operative engagement with distal end 350b of housing 350 to operably retain pusher assembly 360A within housing 350.

In the first or initial position, pusher assembly 360A is prevented from inadvertent distal advancement relative to housing 350 through engagement of the plurality of paired detents 368a, 368b formed on distal portion 364 of pusher adaptor 360 with openings 359 formed in outer cylindrical portion 352 of housing 350.

Figure 21:
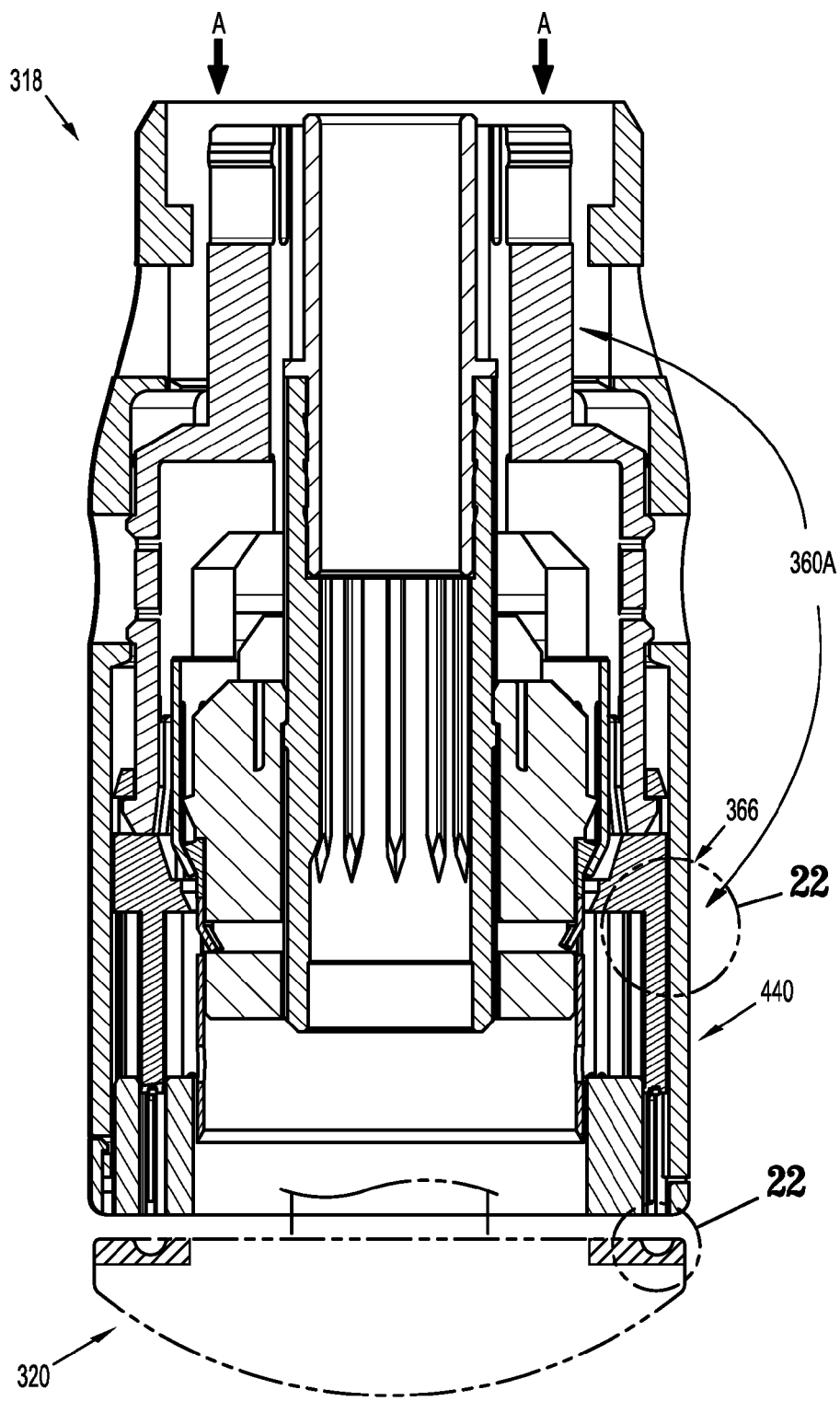
FIG. 21 is the cross-sectional view of FIG. 20, with the surgical fastener applier being actuated.

With reference now to FIGS. 17, 18, and 21, during a first stroke of surgical fastener applier 310, anvil assembly 320 is approximated toward cartridge assembly 318. During a second or firing stroke of surgical fastener applier 310, retraction or actuation of trigger 334 relative to handle 332 causes advancement of a drive assembly (not shown) which operably engages pusher adaptor 360 to cause the advancement of pusher assembly 360A, as indicated by arrows "A". Advancement of pusher adaptor 360 advances pusher member 364 thereby causing pusher members 440 on distal portion 367 thereof to be advanced into surgical fastener receiving pockets 372 of surgical fastener cartridge 370 and to eject surgical fasteners 120 from surgical fastener cartridge 370. The ejection of surgical fasteners 120 from surgical fastener cartridge 370 causes advancement of surgical fasteners 120 into anvil assembly 320 of anvil to form the surgical fasteners 120, thereby securing tissue between the surgical fastener cartridge 370 and anvil assembly 320.

Figure 22:
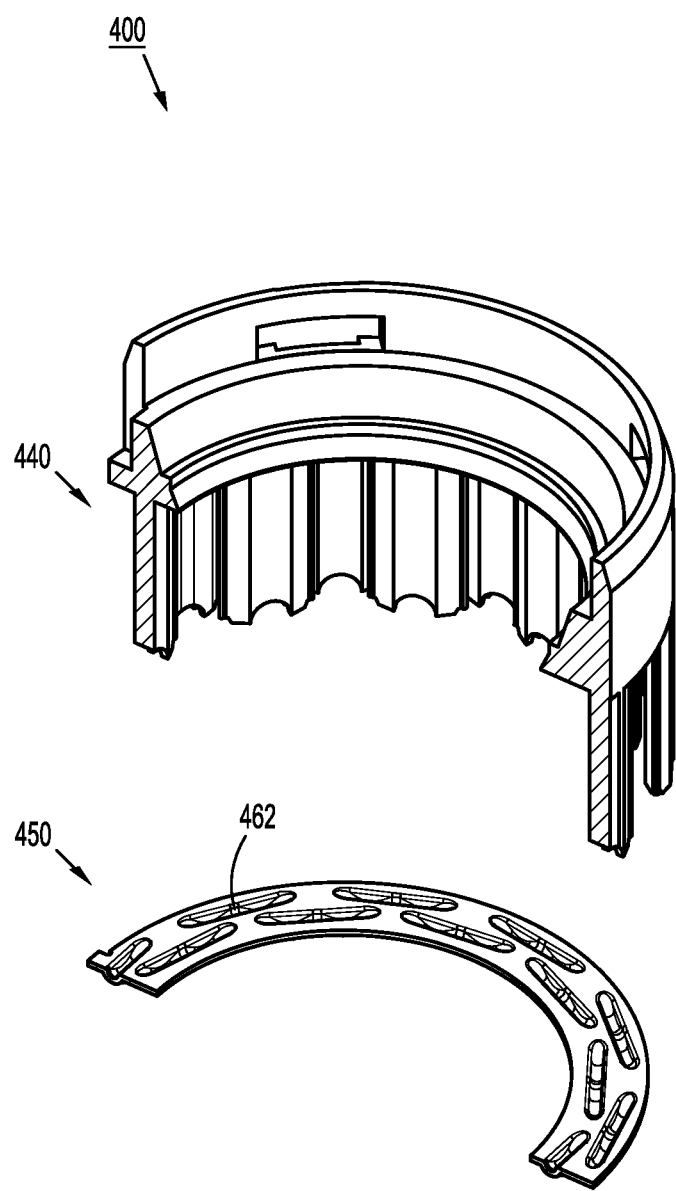
FIG. 22 is an enlarged cut-away view of the area of detail of FIG. 21.

The formation of surgical fasteners 120 by surgical fastener applier 310 will now be described. Turning to FIG. 22, a fastener forming apparatus 400 is shown. Fastener forming apparatus 400 is integrated into the cartridge assembly 318 (FIG. 17) and anvil assembly 320 (FIG. 17) of surgical fastener applier 310 (FIG. 17), and includes the opposed pushers 440 and fastener deforming cavities 462. An anvil portion 450 of anvil assembly 320 is defined by a section of anvil assembly 320 containing a pair of fastener deforming cavities 462, as shown. Fastener forming apparatus 400 is similar to fastener forming apparatus 100 (FIG. 5) discussed above, and may have an arcuate profile for use with surgical fastener applier 310. Fastener forming apparatus 400 will hereafter be discussed with respect to a single pusher 440, opposing a section of anvil portion 450 containing a pair of fastener deforming cavities 462 for clarity.

Referring back to FIGS. 11 and 12, surgical fastener 120 is shown supported by a pusher 440 and opposing a section of anvil portion 450 containing a pair of fastener deforming cavities 462. Pusher 440 contains a groove 442 for supporting backspan 122. Groove 442 is shaped to accommodate the profile of backspan 122, and will retain the backspan 122 upon motion or moderate lateral shifting, but will disengage from backspan 122 when translated away from backspan 122.

A forming head 444 is laterally spaced from groove 442 and extends from the surface of pusher 440. Forming head is configured as a protruding member, as shown in FIGS. 11 and 12. Forming head or protruding member 444 includes at least one curved portion 446 (for example, two curved portions 446 are shown) that engage legs 126 upon fastener formation, as will be described further below. Curved portion 446 extend partially through the proximal portion of pusher 440 such that the distal portion of curved portion 446 approach the distal surface of groove 442. The distal portions of curved portion 446 lie substantially level with the groove 442 such that the distal portions of curved portion 446 lie coplanar with and parallel to the backspan 122.

The fastener deforming cavities 462 of anvil portion 450 receive legs 126 of surgical fasteners 120. Fastener deforming cavities 462 have a first end 464 and a second end 166. Fastener deforming cavities 462 generally have an arcuate profile, though may have any shape or configuration to accommodate the desired fastener formation. The arcuate profile of fastener deforming cavities 462 is such that the first end 464 of each cavity 462 is opposed to a respective curve 446.

As described above, actuation of handle assembly 330 (FIG. 17) causes pushers 440 to advance distally through cartridge assembly 320 and eject surgical fasteners 120 distally to penetrate tissue T and enter fastener deforming cavities 462 such that that legs 126 deform in a manner defined by the profile of fastener deforming cavities 462. Tips 128 (FIG. 8) ultimately exit the second end 466 of cavities 162.

Referring to FIGS. 12 and 13, the deformation of fastener 120 is shown. As the pusher 440 and anvil section 450 are drawn together, the tips 128 and portions of legs 126 again penetrate tissue T and engage curved portion 446 and further deform away from forming head 444. As the legs 126 approach the proximal portion of the curved portion 146, they diverge and approach the ends of backspan 122. Referring back to FIG. 10, upon formation, legs lie parallel to and abut a portion of the backspan 122 in the plane H.

Further aspects of the present disclosure are described in the following numbered paragraphs:

1. A surgical fastener forming apparatus comprising: a surgical fastener including; a backspan having a bend along its length, the backspan and bend defining a flat plane; at least one leg extending from the backspan; a forming structure including; an anvil having at least one cavity to receive the at least one leg; and a pusher including a protruding member; wherein the anvil and protruding member cooperate such that a portion of the at least one leg deforms to lie parallel to and abut a portion of the backspan in the horizontal plane.

2. The surgical fastener forming apparatus of paragraph 1, wherein the at least one cavity has an arcuate profile.

3. The surgical fastener forming apparatus of paragraph 2, wherein the protruding member has at least one curved surface.

4. The surgical fastener forming apparatus of paragraph 1, wherein the pusher includes a groove for receiving the backspan.

5. The surgical fastener forming apparatus of paragraph 1, wherein the at least one cavity and protruding member are disposed on opposing surfaces.

6. The surgical fastener forming apparatus of paragraph 1, wherein the bend in the backspan defines the space within which the at least one leg is disposed after formation.

7. The surgical fastener forming apparatus of paragraph 1, wherein a portion of the at least one leg is configured to penetrate tissue.

8. The surgical fastener forming apparatus of paragraph 7, wherein the distal end of the at least one leg has a surface geometry configured to engage a portion of the backspan.

9. The surgical fastener forming apparatus of paragraph 8, wherein the backspan includes a receiving surface to engage the surface geometry of the distal end of the at least one leg.

10. The surgical fastener forming apparatus of paragraph 1, wherein the fastener has a first leg and a second leg.

11. The surgical fastener forming apparatus of paragraph 10, wherein the bend of the backspan defines an area that accommodates a free end of the first leg and a free end of the second leg after the fastener has been formed.

12. The surgical fastener forming apparatus of paragraph 11, wherein the protruding member defines a curved surface for receiving the free end of the first leg, and a curved surface for receiving the free end of the second leg, the curved surface for receiving the free end of the first leg facing in an opposite direction from the curved surface for receiving the free end of the second leg.

13. The surgical fastener forming apparatus of paragraph 12, each of the curved surfaces including a portion that lies substantially level with a groove of the pusher.

It will be understood that various modifications may be made to the embodiments disclosed herein. For example, the above described surgical fastener may be formed from any of a variety of surgically acceptable materials including titanium, plastics, resorbable materials, etc. Therefore, the above description should not be construed as limiting, but merely as exemplifications of preferred embodiments. Those skilled in the art will envision other modifications within the scope and spirit of the claims appended hereto.

What is claimed is:

1. A surgical fastener forming apparatus comprising:
  a surgical fastener including;
    a backspan having a bend along its length, the backspan and bend defining a flat plane;
    at least one leg extending from the backspan, the at least one leg including a tip configured to penetrate tissue; and
  a forming structure including:
    an anvil having at least one cavity to receive at least a portion of the at least one leg; and
    a pusher including at least one curved portion configured to direct the tip of the at least one leg toward the backspan, the pusher including a backspan-engaging surface that is parallel to the plane defined by the backspan and the bend, and the pusher including a head that protrudes perpendicularly from the backspan-engaging surface toward the anvil;
  wherein the anvil and the at least one curved portion cooperate such that a portion of the at least one leg deforms to lie within the plane defined by the backspan and the bend and to abut a portion of the backspan.

2. The surgical fastener forming apparatus of claim 1, wherein the at least one cavity has an arcuate profile.

3. The surgical fastener forming apparatus of claim 1, wherein the pusher includes a groove for receiving the backspan.

4. The surgical fastener forming apparatus of claim 3, wherein the at least one curved portion is disposed at least partially within the groove.

5. The surgical fastener forming apparatus of claim 1, wherein the at least one cavity and the at least one curved portion are disposed on opposing surfaces.

6. The surgical fastener forming apparatus of claim 1, wherein a distal most end of the at least one leg is configured to be disposed within the plane defined by the backspan and the bend after deformation of the at least one leg.

7. The surgical fastener forming apparatus of claim 1, wherein the tip of the at least one leg has a surface geometry configured to engage a portion of the backspan.

8. The surgical fastener forming apparatus of claim 7, wherein the backspan includes a receiving surface to engage the surface geometry of the tip of the at least one leg.

9. The surgical fastener forming apparatus of claim 1, wherein the head of the pusher is configured to engage the at least one leg of the surgical fastener.

* * * * *